United States Patent [19]
Catalucci

[11] 4,094,874
[45] June 13, 1978

[54] PROCESS FOR THE PRODUCTION OF 2-AMINO-4-HYDROXY-6-METHYLPTERI-DINE

[75] Inventor: Enrico Catalucci, Visp, Switzerland

[73] Assignee: Lonza, Ltd., Gampel, Switzerland

[21] Appl. No.: 759,047

[22] Filed: Jan. 13, 1977

[30] Foreign Application Priority Data

Jan. 13, 1976 Switzerland .......................... 313/76

[51] Int. Cl.² ............................................ C07D 475/04
[52] U.S. Cl. ...................................................... 544/258
[58] Field of Search ........................................ 260/251.5

[56] References Cited
PUBLICATIONS

King et al., J. Chem. Soc., 1952 pp. 2144–2152.

*Primary Examiner*—Paul M. Coughlan, Jr.
*Attorney, Agent, or Firm*—Fisher, Christen & Sabol

[57] ABSTRACT

The process for the production of 2-amino-4-hydroxy-6-methylpteridine from 2,4,5-triamine-6-hydroxypyrimidine and 1,1-dichloroacetone which is characterized in that the 2,4,5-triamino-6-hydroxypyrimidine in the form of one of its stable salts is converted with 1,1-dichloroacetone. The 1,1-dichloroacetone is present in a 1 to 2 equivalents ratio, based upon the 2,4,5-tiramino-6-hydroxypyrimidine, to 2-amino-4-hydroxy-6-methylpteridine. The conversion is conducted in a solvent at a pH of 3.5 to 4.5 in the presence of sodium bisulfite. From 1.2 mole of the sodium bisulfite per mole of the stable salt of 2,4,5-triamino-6-hydroxypyrimidine at 5 liters of reaction solution up to 3 moles of sodium bisulfite per mole of the stable salt of 2,4,5-triamino-6-hydroxypyrimide at 50 liters of reaction solution is used.

11 Claims, No Drawings

PROCESS FOR THE PRODUCTION OF 2-AMINO-4-HYDROXY-6-METHYLPTERIDINE

BACKGROUND OF THIS INVENTION

1. Field of this Invention

This invention relates to a process for the production of 2-amino-4-hydroxy-6-methylpteridine from 2,4,5-triamino-6-hydroxypyrimidine and 1,1-dichloroacetone.

2. Prior Art

The production of 2-amino-4-hydroxy-6-methylpteridine via 2-amino-4-chloro-5-phenylazo-6-hydroxypyrimidine [Boon, Leigh, J. Chem. Soc., (1951), 1497] or via pyrazine derivatives [Taylor, J.A.C.S., 95, 6407, (1973)] free of isomers. These processes are however uneconomical since they are based on several, in part complicated, synthesis steps.

Other production methods are based on the cyclization of 2,4,5-triamino-6-hydroxy pyrimidine, made from quanidine and ethylcyanoacetate with acetoxyacetone [Viscontini, Helv. Chim. Acta, 54, 811 (1971)] or pyruvate aldehyde [U.S. Pat. No. 2,477,426 and Storm, J. Org. Chem., 36, 3925 (1971)]. The acetoxyacetone and pyruvate aldehyde however are extremely unstable and therefore can be used only with difficulty in the execution of the reaction. In the case of such processes there is the additional difficulty thatmixtures of almost unseparable 6- and 2-amino-4-hydroxy-7-methylpteridine result.

Another process [King, Spensley, J. Chem. Soc., 2144, (1952)] describes the production of 2-amino-4-hydroxy-6-methylpteridine by reaction of 2,4,5-triamino-6-hydroxypyrimidine with 1,1-dichloroacetone. However, when such process was conducted by applicant, mostly undesirable 2-amino-4-hydroxy-7-methylpteridine was obtained.

BROAD DESCRIPTION OF THIS INVENTION

An object of this invention is to create a process for the production of isomer-free 2-amino-4-hydroxy-6-methylpteridine in good yields from easily producible starting materials. Other objects and advantages of this invention are set out herein or are obvious herefrom to one ordinarily skilled in the art.

The objects and advantages of this invention are achieved by the process of this invention.

The process of this invention involves converting 2,4,5-triamino-6-hydroxypyrimidine in the form of one of its stable salts with 1,1-dichloroacetone, such being present in a 1 to 2 times equivalents quantity, to 2-amino-4-hydroxy-6-methylpteridine. The conversion is conducted in a solvent or a mixture of solvents at a pH value of 3.5 to 4.5 in the presence of sodium bisulfite.

Also, from 1.2 mole of sodium bisulfite per mole of the pyrimidine compound at 5 liters of reaction solution up to 3 mole of sodium bisulfite per mole of the pyrimidine compound at 50 liters of reaction solution is used.

Schematically, the reaction of the process is illustrated as follows:

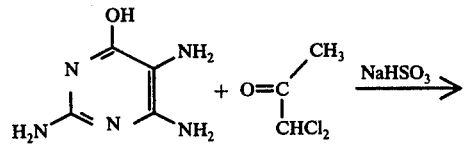

-continued

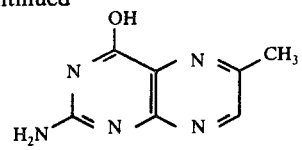

According to the process of this invention, the 2,4,5-triamino-6-hydroxypyrimidine is used in the form of one of its stable salts, preferably, the hydrochloride or sulfate. The reaction is carried out in a solvent or solvent mixture; water may be used as the solvent, or water with a water-soluble solvent, preferably, ethanol or dimethyl formamide, may be used as the solvent mixture.

The pH value of the reaction solution must remain constant during the reaction and must have a value of 3.5 to 4.5. The preferred pH value of the reaction solution is 4.0.

In order to keep the pH value constant during the reaction, a solution of NaOH or of some other base, inert vis-a-vis dichloro acetone, such as, $NaHCO_3$, in any concentration may be dosed in, or otherwise a buffer, for example, $NaOCOCH_3/CH_3COOH$, may also be used.

The temperature of the reaction mixture may vary from 10° C. up to its boiling point although preferably operation is between 25° and 80° C.

The reaction is carried out in such a way that the pyrimidine compound is placed in the solvent, dissolved in the solvent or suspended in the solvent, is heated to the reaction temperature and is adjusted to the pH value of this invention by adding a base or bases. The quantitiy of sodium bisulfite must amount to at least 1 mole per mole of the pyrimidine compound.

The quantity of sodium bisulfite should be increased with any increasing dilution of the pyrimidine in the solvent.

According to the process of this invention, 1.2 mole of sodium bisulfite per mole of the pyrimidine compound at 5 liters of reaction solution up to 3 mole of sodium bisulfite per mole of the pyramidine compound at 50 liters of reaction solution is used.

2-amino-4-hydroxy-6-methylpteridine is important as an intermediate in the synthesis of higher derivatives and especially of folic acid (see U.S. Pat. Nos. 2,584,538, 2,547,519 and 2,547,520).

DETAILED DESCRIPTION OF THIS INVENTION

As used herein, all parts, proportions and percentages are on a weight basis unless otherwise stated or obvious herefrom to one ordinarily skilled in the art.

EXAMPLE 1

The reaction (conversion) was carried out in a 100 ml breaker having a magnetic stirrer thermometer, a pH-electrode and a thermo-regulated water bath, with constant stirring. The dosing of the inorganic base was accomplished automatically and continuously. 40 ml of $H_2O$ was placed in the 100 ml beaker. 2.50 gm of 2,4,5-triamino-6-hydroxypyrimidime sulfate, 96 percent, (1 × $10^{-2}$ mole), was then mixed with the water. The solution was heated to 40° C. and a pH value of 4 was reached in a few minutes by the addition of about 10 ml of 1N NaOH. Immediately after that 1.1 gm. of sodium metabisulfite (corresponding to 1.2 × $10^{-2}$ mole of NaHSO₃) was added. Stirring was continued for 5 to 10 minutes. Then 2.0 gm. of 1,1-dichloro acetone, 98 percent (1.5 × 10⁻² mole), was added in one administration. Stirring was continued at 40° C., while the pH value was kept constant at 4 by the automatic addition of 1N NaOH. After about 0.5 hours, about 20 ml of 1N NaOH had been consumed and the reaction was completed. The precipitated product was isolated by filtration, washed with about 20 ml of water and dried at 110° C./30 torr. 0.92 gm. (52 percent of theory, based on the amount of pyridimine used) of an orange powder were obtained, which according to thin-layer-electrophoresis and elementary analysis was pure. The NMR spectrum in CF₃COOH (TMS as standard) only showed the following peaks:

$\delta = 8.93-8.96$   s (1H) arom. H
$\delta = 8.5-9.0$   s (2H) amino group
$\delta = 2.93$   s (3H) methyl group Through NMR in FSO₃H (TMS as ext. standard) the quantity of the 7-isomer was determined by the proportion (ratio) of the following peaks:

$\delta = 8.76-8.82$   s (IH) arom. H of 2-amino-4-hydroxy-7-methylpteridine
$\delta = 9.46-9.53$   s (1H) arom H of 2-amino-4-hydroxy-6-methylpteridine The quantity of the 7-isomer was less than 5 percent based on the quantity of the 2-amino-4-hydroxy-6-methylpteridine.

EXAMPLE 2

The reaction was carried out in a 10 liter flask having a compressed air stirrer.

First, a solution of 870 gm. of glacial acetic acid and 144 gm. of caustic soda solution in 8 liters of water were prepared in the 10 liter flask. After that, 170 gm. of sodium bisulfite was added. As soon as the sodium bisulfite was dissolved, an additional 120.2 gm. of 2,4,5-triamino-6-hydroxypyrimidine sulfate, 99.5 percent, 0.5 mole), was added. Stirring was conducted for about 30 minutes and then 130 gm. of 1,1-dichloroacetone, 97 percent, (1 mole), was added. Stirring was then conducted at ambient temperatures for 24 hours. After that the product was isolated by filtration and washed with 200 ml of water on the filter. The product subsequently was boiled in 3000 ml of water and the NaOOCCH₃ residue was removed. After filtration at ambient temperature the product was dried at 110° C/30 torr.

43.0 gm (48.5 percent of theory, based on the amount of pyrimidine used) of a product of the same quality as that of Example 1 was obtained.

EXAMPLE 3

In a 100 ml. beaker, having a magnetic stirrer and pH electrode, 2.45 gm. (1.01 × 10⁻² mole) of 2,4,5-triamino-6-hydroxy-pyrimidine hydrochloride, 88.1 percent, (the product was contaminated with BaCl₂) in 60 ml. of H₂O was mixed with 1.7 gm. of sodium metabisulfite. The solution was quickly brought to a pH of 4 by means of the addition of about 10 ml of 1N NaHCO₃.

Subsequently, while stirring, 1.28 gm. of 1,1-dichloro acetone, 99 percent (1 × 10⁻² mole), dissolved in 20 ml of ethanol was added. Stirring was continued for 36 hours at ambient temperature. During this time the pH value was kept between 3.5 and 4.3 by periodic, discontinuous additions of 1N NaHCO₃. The amount of filtered raw product was 1.2 gm. (68 percent of theory, based on the amount of dichloroacetone used). The filtered raw product was free of isomers, according to NMR and, according to elementary analysis, still contained 6.4 percent of sodium chloride.

EXAMPLE 4

The apparatus described in Example 1 was used (with continuous stirring). 2.47 gm. of 2,4,5-triamine-6-hydroxy pyrimidine sulfate, 97 percent, (1 × 10⁻² mole), was brought to a pH of 4 at ambient temperature by adding about 10 ml of 1N NaOH. Subsequently, 1.5 gm of sodium metabisulfite was added and heated to 80° C. Then 1.5 gm. of 1,1-dichloro acetone, 95 percent, (1.1 × 10⁻² mole), was added. The pH value was kept constant at 4 by the automatic addition of 1N NaOH. The reaction was finished after 0.5 hour. The reaction mixture was processed as in Example 1 and 0.78 gm. of 2-amino-4-hydroxy-6-methylpteridine (44 percent of theory, based on the amount of pyrimidine used) was obtained. According to NMR in CF₃COOH and FSO₃H, the product was pure and free of isomers.

EXAMPLE 5

In an enamelled agitator, having a 50 liter capacity, a solution of 3.480 kg of glacial acetic ester and 0.570 kg of NaOH solid in 32 liters of water was prepared. 0.68 kg of sodium metabisulfite was added to the mixture. After the sodium metabisulfite dissolved, 0.527 kg of 2,4,5-triamino-6-hydroxypyrimidine sulfate, 71 percent, (2 mole), were added. The material was stirred for 1 hour at ambient temperature. Subsequently, 0.142 kg of 95 percent and 0.132 kg of 97 percent 1,1-dichloro acetone (2 mole) were added. Stirring was continued at ambient temperature for 63 hours. Subsequently, the methylpteridine was isolated by filtration and was washed with 12 liters of boiling water for 30 minutes. After cooling and repeated filtration, 0.181 kg of product (51 percent of theory, based on the amount of pyrimidine used) was obtained. According to NMR, the product was free of acetate and isomers.

What is claimed is:

1. The process for the production of 2-amino-4-hydroxy-6-methylpteridine from 2,4,5-triamine-6-hydroxypyrimidine and 1,1-dichloroacetone which is characterized in that the 2,4,5-triamino-6-hydroxypyrimidine in the form of one of its stable salts is converted with 1,1-dichloro acetone, such being present in a 1 to 2 times equivalent quantity, in relation to said 2,4,5-triamino-6-hydroxypyrimidine, to 2-amino-4-hydroxy-6-methylpteridine, in a solvent of solvent mixture at a pH value of 3.5 to 4.5 in the presence of sodium bisulfite, from 1.2 mole of said sodium bisulfite per mole of said stable salt of 2,4,5-triamino-6-hydroxypyrimidine at 5 liters of reaction solution up to 3 moles of the sodium bisulfite per mole of said stable salt of 2,4,5-triamino-6-hydroxypyrimidine at 50 liters of reaction solution being used.

2. The process as claimed in claim 1 wherein said stable salt of 2,4,5-triamino-6-hydroxypyrimidine is the hydrochloride or sulfate of 2,4,5-triamino-6-hydroxypyrimidine.

3. The process as claimed in claim 1 wherein said solvent mixture is water with a water-soluble solvent.

4. The process as claimed in claim 3 wherein said water-soluble solvent is ethanol or dimethyl formamide.

5. The process as claimed in claim 1 wherein said solvent is water.

6. The process as claimed in claim 1 wherein a pH value of 4.0 is used in said conversion.

7. The process as claimed in claim 1 wherein said sodium bisulfite is sodium metabisulfite.

8. The process as claimed in claim 1 wherein said pH value is kept constant during said conversion by the addition of a base as needed to keep said pH value constant.

9. The process as claimed in claim 8 wherein said base is NaOH or $NaHCO_3$.

10. The process as claimed in claim 1 wherein said pH value is kept constant during said conversion by the addition of a base and a buffer as needed to keep said pH value constant.

11. The process as claimed in claim 10 wherein said buffer is $NaOCOCH_3/CH_3COOH$.

* * * * *